United States Patent [19]

Macek et al.

[11] Patent Number: 5,853,715
[45] Date of Patent: Dec. 29, 1998

[54] CROSS-PROTECTIVE EQUINE HERPESVIRUS PREPARATIONS AND METHOD OF MAKING AND USING THE SAME

[75] Inventors: Joseph Macek, Paola, Kans.; Karen K. Brown, Parkville, Mo.; Bobby O. Moore, Merriam, Kans.

[73] Assignee: Bayer Corporation, Pittsburgh, Pa.

[21] Appl. No.: 698,630

[22] Filed: Aug. 16, 1996

[51] Int. Cl.$^6$ .................................................. A61K 35/12
[52] U.S. Cl. ......................................................... 424/93.1
[58] Field of Search ............................................ 424/93.1

[56] References Cited

U.S. PATENT DOCUMENTS

| | | | |
|---|---|---|---|
| 4,083,958 | 4/1978 | Bryans | 424/89 |
| 4,110,433 | 8/1978 | Purdy, III | 424/229.1 |
| 4,225,582 | 9/1980 | Crandell | 424/229.1 |
| 5,084,271 | 1/1992 | Studdert | 424/89 |

FOREIGN PATENT DOCUMENTS

| | | |
|---|---|---|
| 2053829 | 4/1992 | Canada . |
| 310317 | 4/1989 | European Pat. Off. . |
| 532833 | 3/1993 | European Pat. Off. . |
| 0668355 | 8/1995 | European Pat. Off. . |
| 0491125 | 4/1996 | European Pat. Off. . |
| 95/22607 | 8/1995 | WIPO . |

OTHER PUBLICATIONS

J. Ellis et al., Journal of the American Veterinary Medical Association, vol. 206, No. 6, Mar. 15, 1995, pp. 823–832 (XP002053533).

N. Edington et al., Research in Veterinary Science, vol. 48, No. 2, Mar. 1990, pp. 235–239 (XP002053534).

D. Love et al., Journal of Virology, vol. 67, No. 11, Nov. 1993, pp. 6820–6823. (XP002053535).

D. Fitzpatrick et al., American Journal of Veterinary Research, vol. 45, No. 10, Oct. 1984 pp. 1947–1952, XP002053536.

A. Stokes et al., Research in Veterinary Science, vol. 51, No. 2, Sep. 1991, pp. 141–148, XP002053537.

*Primary Examiner*—Peter F. Kulkosky
*Attorney, Agent, or Firm*—Joseph C. Gil; Godfried R. Akorli

[57] ABSTRACT

Disclosed herein is an EHV-1 vaccine which provides protection against diseases associated with EHV-1 and EHV-4, and methods of preparing and using the same.

12 Claims, No Drawings

CROSS-PROTECTIVE EQUINE HERPESVIRUS PREPARATIONS AND METHOD OF MAKING AND USING THE SAME

This invention relates to the discovery of an Equine Herpesvirus preparation which protects against abortion and respiratory disease caused by Equine Herpesvirus type 1 and respiratory disease caused by Equine Herpesvirus type 4. More specifically, this invention relates to a efficacious vaccine, and methods of making and using the same.

BACKGROUND OF THE INVENTION

Equine abortion and equine rhinopneumonitis are commonly recognized diseases attributed to Equine Herpesvirus types I (EHV-1) and 2. Equine Herpesvirus type 2 is now designated EHV-4 as the molecular structure has been determined to be significantly different from EHV-1. EHV-1 is mainly responsible for causing respiratory disease. The economic losses consequent to respiratory disease produced by either subtype of EHV in young horses result from inability or impaired ability to perform in competition. The economic losses resulting from infection of pregnant mares are due to abortion. A central nervous system syndrome has also been associated with EHV-1, such disease progresses from ascending paralysis to complete paralysis and, in some instances, to death.

Because of the lack of homology between EHV-1 and EHV-4, it has been proposed that only an equine herpesvirus vaccine which contained both subtypes EHV-1 and EHV-4 would protect from abortion and the various forms of respiratory disease. Indeed, U.S. Pat. No. 4,083,958 describes an equine herpesvirus vaccine which protects only against abortion and respiratory disease caused by EHV-1. It does not claim to protect against respiratory disease caused by EHV-4. U.S. Pat. No. 5,084,271 states that exposure of foals to EHV-1, whether live or inactivated, produces an antibody response only to EHV-1. Exposure of foals to EHV-4 produces a serological response to both EHV-1 and EHV-4. However, no actual protection against challenge was shown. The latter patent claims that an effective vaccine must contain EHV-4 alone or a combination of EHV-1 and EHV-4. Thus, a monovalent EHV-1 vaccine would not be expected to protect against EHV-1 and EHV-4 respiratory syndromes as well as from abortion caused by EHV-1.

SUMMARY OF THE INVENTION

The present invention encompasses an Equine Herpesvirus subtype 1 (EHV-1) strain designated herein as AB69 or an equivalent thereof that is useful in the preparation of antigens for induction of protective immune response to EHV-1 and EHV-4. Also encompassed by the invention is a preparation such as a monovalent vaccine containing the AB69 that can be used to vaccinate either young foals, adult equines or pregnant mares to provide protection from respiratory disease caused by either EHV-1 or EHV-4 and also, provide protection against abortion due to EHV-1.

Further encompassed by the invention is the method of making the preparation and using the same to protect horses. It is envisioned that vaccine preparations of this invention can also provide protection from incidences of central nervous system disease caused by EHV-1.

In the present embodiment, the invention encompasses the process for preparing such a monovalent EHV-1 vaccine by propagating the strain AB69 or an equivalent thereof in a continuous cell culture, harvesting and purifying by removing cell debris from the virus supernatant, concentrating, chemically inactivating and adjuvanting as described more fully hereunder.

DETAILED DESCRIPTION OF THE INVENTION

As set forth above, the present invention relates to an EHV-1 virus which, when made into a preparation such as a vaccine and administered parenterally to horses, provides protection of all horses from the diseases associated with EHV-1 and EHV-4. More specifically, the disclosed EHV-1 vaccine provides protection to pregnant mares against abortion caused by EHV-1, protects horses from respiratory disease caused by either EHV-1 or EHV-4 and reduces the incidence of central nervous system disease caused by EHV-1. The EHV-1 virus strain useful for preparation of this vaccine was isolated from the infected lung tissue of an aborted fetus during a challenge study. The isolate, designated AB69, has been deposited with the ATCC as accession number ATCC VR 2581. The virus was passaged twice on an Equine Dermal Cell Line to establish a Master Seed. The virus can be grown on susceptible cell lines which effectively replicate the virus to a level sufficient to provide an amount sufficient (antigenic mass) to be immnogenically sufficient to provide protection against EHV-1 and EHV-4. The following is a non-limiting but illustrative description of a method of replicating the virus and making a vaccine therewith.

The method comprises the steps of 1) infecting a susceptible cell line with an EHV-1 virus; 2) allowing said EHV-1 virus to grow in a growth-supporting media until a significant cytopathic effect (CPE) is produced; 3) harvesting said growth-supporting media containing said EHV-1 virus, dead cells, cell debris and infected cells to produce a harvest material; 4) inactivating said harvest material with a suitable inactivating agent; and 5) adjuvanting said inactivated harvest material. The susceptible cell line is preferably of equine origin, more preferably an Equine Dermal Cell Line, an Equine Kidney Cell Line or a Fetal Equine Lung Cell Line. This cell line is used to grow the EHV-1 strain to high titers. The cell line can be grown in Roux bottles, roller bottles or in bioreactors as a suspension culture or on microcarrier beads using any media and serum that supports rapid growth of the cells. The preferred media are Earle's or Hank's Minimal Essential Media (MEME and MEMH, respectively) with glutamine and non-essential amino acids added. The preferred sera for cell growth are fetal equine, fetal bovine or calf serum. The cell line is grown to confluency and then infected with the EHV-1 virus with a multiplicity of infection (MOI) shown to produce maximum infectious virus particle yields of virus per milliliter of media. Preferably, this MOI is between 0.0001 and 1.0. The infected cell line is allowed to grow until the cells show a significant cytopathic effect (CPE). A significant CPE is defined as a >80% destruction of the cells as microscopically visualized by dead cells sloughing off of the surface of the growth vessel of the microcarrier beads. The media containing infected cells, dead cells, cell debris and EHV-1 is harvested by removing it from the vessels in which it is grown and transferring it to holding vessels such as tanks or bags. This harvest material is purified by filtration or centrifugation to remove the cells and cell debris after which the supernatant fluids are concentrated by ultrafiltration, ultracentrifugation or column chromatography. The concentrated fluids are inactivated by addition of any inactivating agent which will preserve the antigenicity of the virus. The preferred inactivating agents are beta propriolactone, formalin or binary ethylenimine. Preservatives such as thimerosal can be added to the inactivated fluids. After inactivation, the inactivated material is adjuvanted. Any number of adjuvants can be used including, but not limited to: Carbopol 934P®, Havlogen®, Polygen™, block copolymers, polymers, oils, aluminum salts such as aluminum hydroxide and aluminum phosphate, cytokines and immunomodulators and combinations thereof. After adjuvanting, stabilizers such as glycerol/EDTA can be added to improve antigen stability.

As would be realized by those skilled in the art, once the virus can be propagated as afore-described, derivatives thereof including subunits can be obtained by means known in the art such as extraction from the virus. Additionally, the protective antigens can be identified at molecular level and reproduced and expressed using recombinant technology.

The invention is further illustrated but is not intended to be limited by the following examples in which all parts and percentages are by weight unless otherwise specified.

EXAMPLES

Example 1

An Equine Dermal Cell Line grown to approximately 90% confluency in 1750cm$^2$ roller bottles using MEME+ 10% fetal calf serum. The confluent cells were infected with an EHV-1 strain designated AB69 and transferred into (MEME) containing non-Essential Amino Acids, Glutamine, Neomycin Sulfate and (Polymyxin B). The infected cell cultures were incubated at 37° C. for three to six days or until there was 90–95% CPE after which the cells and fluids were aseptically harvested into a single container. The harvest was then clarified by filtration through a 5 $\mu$ filter and concentrated five-fold using ultra-filtration through a 100,000 MW cartridge. The concentrated fluids were inactivated by adjusting the pH to between 8.0 to 8.3, adding Beta propiolactone to a final concentration between 0.05 and 0.15% and incubating at 37° C. for three to six hours while controlling the pH between 6.8 and 7.2 with 10N NaOH. The latter incubation period hydrolyzed the Beta propiolactone. After inactivation was complete, the fluids were adjuvanted by the addition of Havlogen®, and thimerosal was added as a preservative to complete vaccine production. The vaccine produced by this process was designated EHV-1 MHD 91-001.

A vaccination/challenge study was conducted to determine whether the EHV-1 MHD 91-001 vaccine could protect pregnant mares from EHV-1 respiratory disease and from abortion caused by equine herpesvirus. During this study, forty-five mares in the second trimester of pregnancy (average was 5th month of pregnancy) were separated into two groups. One group containing 22 pregnant mares was designated non-vaccinated controls. The second group of 23 mares were vaccinated with 2.0 mL of the EHV-1 MHD 91-001 during the 5th, 7th, and 9th months of pregnancy. For the respiratory challenge the vaccinate group contained 22 mares as one mare died post challenge after slipping and breaking her back. For the abortion challenge, the vaccinate group contained only 19 pregnant mares by the end of the challenge period (one mare aborted early in the study, the one mare died post challenge after slipping and breaking her back and two mares known to be open at the beginning of the trial were randomly assigned to the vaccinate group at the first day of vaccination).

All mares were challenged (whether they were pregnant or not as the non-pregnant mares could still be used for the respiratory challenge). The mares were sedated with Rompun®, available from Bayer Corporation, prior to challenge. Each mare was then challenged with early passage AB69 at a dose rate of approximately 10$^{5.0}$ TCID$_{50}$. This challenge was delivered intranasally utilizing a nebulizer which produced a fine aerosol which forced the virus into the lungs. The challenge virus and procedure had been shown to produce abortion and respiratory disease in pregnant mares in previous challenge titration studies.

Post challenge, all mares were placed into enclosed pens wherein they could be observed for signs of respiratory disease and abortion. In order to determine the protection from respiratory disease mares were observed and sampled daily for 11 days, post-challenge. Daily post-challenge observation of all mares included evaluation and scoring for the clinical signs of respiratory disease including nasal discharge (exudate) and elevated rectal temperature. Additionally, blood samples were taken daily. White blood cell counts were measured and virus isolation was attempted from the buffy coats separated from the daily blood samples. Also, on each test day, the nasal passages of each mare were swabbed, with the swabs placed into transport media for later virus isolation attempts. In order to determine the protection from abortion, all live foals, dead foals and aborted fetuses were analyzed for indications of EHV-1 infection. Blood samples and necropsy tissue samples were collected for attempts at virus isolation. Results of the respiratory evaluation are shown in Tables 1a, 1b and 1c. Results of the abortion evaluation are shown in Table 2.

As shown in Table 1a, the vaccinated mares showed a 96.1% reduction in virus shedding from nasal exudates as compared with non-vaccinated control mares. Following EHV-1 aerosol challenge inoculation, EHV-1 virus was recovered from the nasal swabs collected from the vaccinates on only 2 of 242 (9.826%) of isolation attempts, whereas, EHV-1 virus was recovered from 51 of 242 (21.07%) of the swabs collected from non-vaccinated control mares.

As demonstrated in Table 1b, the temperature response of vaccinated mares post challenge was significantly less than that of the control mares on post challenge observation day 2. On this day, all of the vaccinates displayed normal rectal temperatures (98.0°–100.9° C.) and 13 of 22 (59.09%) of the non-vaccinated control mares displayed elevated rectal temperatures (101° C. or greater).

The severity of the EHV-1 respiratory disease in the non-vaccinated control mares was further indicated by their post challenge nasal exudate scores. As noted in Table 1c, individual daily nasal exudate scores of greater than or equal to 4 are indicative of a significant level of respiratory disease. Two of 22 vaccinated mares (9.09%) and 9 of 22 (40.09%) non-vaccinated control mares developed this level of disease. This difference between respiratory disease in the vaccinated mares as compared with the control mares is statistically significant ($p<0.03$).

The severity of the EHV-1 respiratory disease in the non-vaccinated control mares was further indicated by the trends shown in their post challenge white blood cell counts (WBC) which are not shown. Between day 2 and day 5 post challenge, the non-vaccinated control mares showed a more pronounced depression of their mean WBCs than the vaccinated mares.

In summary, the EHV-1 monovalent vaccine containing only an EHV-1 strain showed significant protection from EHV-1 induced respiratory disease as compared with non-vaccinated control mares post challenge.

TABLE 1a

EHV-1 Respiratory Disease -- Virus Isolation from Nasal Swabs
DAYS POST CHALLENGE
Number of Observation Days of Virus Shedding Post Challenge

| GROUP | −2 | −1 | 0 | 1 | 2 | 3 | 4 | 5 | 6 | 7 | 8 | 9 | 10 | 11 | No. Pos./ Total No. Days |
|---|---|---|---|---|---|---|---|---|---|---|---|---|---|---|---|
| Vaccinates | 0 | 0 | 0 | 0 | 0 | 1 | 0 | 1 | 0 | 0 | 0 | 0 | 0 | 0 | 2/242* |
| Controls | 0 | 0 | 0 | 0 | 8 | 7 | 7 | 12 | 6 | 6 | 4 | 0 | 1 | 0 | 51/242* |

*No. of possible observations

TABLE 1b

EHV-1 Respiratory Disease -- Temperature above 101° F.
DAYS POST CHALLENGE
Number of Mares With Temperatures Above 101° F. on Each Day

| GROUP | −2 | −1 | 0 | 1 | 2 | 3 | 4 | 5 | 6 | 7 | 8 | 9 | 10 | 11 | No. Pos./Total on Day 2* |
|---|---|---|---|---|---|---|---|---|---|---|---|---|---|---|---|
| Vaccinates | 0 | 0 | 0 | 0 | 0 | 0 | 0 | 0 | 0 | 1 | 2 | 0 | 0 | 0 | 0/22 |
| Controls | 0 | 0 | 0 | 0 | 13 | 2 | 0 | 0 | 0 | 0 | 0 | 0 | 0 | 0 | 13/22 |

*Elevated temperatures on day 2 and 3 post challenge are indicators of clinical signs

TABLE 1c

EHV-1 Respiratory Disease -- Nasal Exudate Score >4
DAYS POST CHALLENGE
Number of Mares with Nasal Exudate Scores >4 For Each Day

| GROUP | −2 | −1 | 0 | 1 | 2 | 3 | 4 | 5 | 6 | 7 | 8 | 9 | 10 | 11 | No. >4* Total No. Mares |
|---|---|---|---|---|---|---|---|---|---|---|---|---|---|---|---|
| Vaccinates | 0 | 0 | 0 | 0 | 1 | 1 | 0 | 0 | 0 | 0 | 0 | 0 | 0 | 0 | 2/22 |
| Controls | 0 | 0 | 0 | 0 | 1 | 3 | 2 | 0 | 2 | 0 | 0 | 0 | 0 | 0 | 8/22 |

Number of different mares with nasal exudate scores equal to or >4 indicates significant clinical signs of disease.

Observation for abortion post challenge was continued after the respiratory observations were completed. As mentioned previously, the mares were randomly placed into pens with two mares per pen. Selection of pen mates was based on compatibility. The mares were observed daily in the morning and evening for any signs of foaling. Whenever a mare foaled a live or dead foal and/or aborted fetus, the following procedure was initiated.

1) In the event that the delivering mare was having a difficult labor, the farm veterinarian assisted in delivery. One mare in the study required assistance.
2) Live Foals—On discovery of a live foal, blood samples were immediately collected for buffy coat virus isolation studies and, if necessary, for serological studies in the event of a neonatal death due to EHV-1.
3) Aborted fetuses and Dead Foals—All aborted fetuses and dead foals were immediately placed in the necropsy room refrigerator to deter autolysis. All post-mortem examinations were made by the farm veterinarian and research staff in charge of the project. All necropsy examinations included the following: a) visual observations of the foal's organs for evidence of gross pathology, b) the collection of blood samples for serological and virus isolation studies; and c) collection of tissue samples from the thymus, lungs, heart, liver, kidney and spleen which were placed in individual containers containing either 10% buffered formalin for histopathology studies or MEME containing a 5× concentration of neomycin and polymycin B for virus isolations.

The summary of mare parturition is shown in Tables 2a and 2b. Tables 2a and 2b include the following information from each vaccinated and non-vaccinated pregnant mare: 1) the mare's number; (2) the mare's calendar foaling date; (3) the day post challenge on which parturition occurred; (4) the type of delivery experienced by each test mare; (5) the foals health status on delivery; and (6) the potential cause of fetal death and/or the infectious virus contributing to the death of the neonate. At the bottom of the Tables, post challenge range and mean parturition days for each test group are listed.

Sixteen of the nineteen pregnant vaccinated mares equalling 84.21%, delivered normal healthy foals post EHV-1 challenge. One vaccinated pregnant mare had problems during attempted delivery of a near term fetus in dorsal transverse presentation. The fetus died during mechanical assisted delivery. This dystocia neonate was found on viral isolation studies to be culture negative for the EHV-1 challenge virus. This foal's death was due neither to vaccine nor to the EHV-1 challenge virus. Two fetuses from vaccinated mares were found to be positive for the EHV-1 virus post challenge. For the non-vaccinated control mares, 15 of 22 (68.20%) delivered normal healthy foals. All 15 normal foals cultured free of EHV-1 challenge virus. However, the EHV-1 virus was isolated from the tissues of all 7 of the aborted or dead neonates in the non-vaccinated control group. Therefore, the vaccinates showed a 67% reduction in the incidence of EHV-1 infected fetuses and neonates as compared with non-vaccinated control mares. This clearly demonstrates the efficacy of the EHV-1 monovalent vaccine related to the protection of pregnant mares from abortion.

This demonstrated that the monovalent EHV-1 vaccine effected a reduction in respiratory disease caused by EHV-1 in vaccinated mares as compared with non-vaccinated control mares. In addition, the monovalent EHV-1 vaccine effected a reduction in abortion or death in neonates from vaccinated pregnant mares as compared with non-vaccinated control pregnant mares in a vaccination/challenge study using EHV-1 as the challenge virus.

TABLE 2a

Parturition Summary for 19 EHV-1 Monovalent Vaccinated Pregnant Mares Following Intranasal Challenge Inoculation with EHV-1 Subtype 1 Virus

| Mare No. | Foaling Date | Days Post Challenge | Type Delivery | Foal Delivery Status | Cause of Death |
|---|---|---|---|---|---|
| 804 | 3-4-92 | 16 | Abnormal | Dead | Dystocia |
| 814 | 3-12-92 | 24 | Abortion | Dead | EHV-1 |
| 837 | 3-27-92 | 39 | Abortion | Dead | EHV-1 |
| 798 | 3-31-92 | 43 | Normal | Live | N/A |
| 832 | 4-5-92 | 48 | Normal | Live | N/A |
| 860 | 4-10-92 | 53 | Normal | Live | N/A |
| 833 | 4-11-92 | 54 | Normal | Live | N/A |
| 818 | 4-13-92 | 56 | Normal | Live | N/A |
| 803 | 4-14-92 | 57 | Normal | Live | N/A |
| 807 | 4-16-92 | 59 | Normal | Live | N/A |
| 835 | 4-18-92 | 61 | Normal | Live | N/A |
| 824 | 4-19-92 | 62 | Normal | Live | N/A |
| 812 | 4/25/92 | 68 | Normal | Live | N/A |
| 862 | 4/27/92 | 70 | Normal | Live | N/A |
| 815 | 4/29/92 | 72 | Normal | Live | N/A |
| 799 | 5-4-92 | 77 | Normal | Live | N/A |
| 813 | 5-5-92 | 78 | Normal | Live | N/A |
| 834 | 5-7-92 | 80 | Normal | Live | N/A |
| 826 | 5-14-92 | 87 | Normal | Live | N/A |

The Mean Days Post Challenge for foaling was 58, the Range varied from 16 to 87 days. Abortions/Deaths due to EHV-1 were 2/19 or 10.5%.
Normal Foals: 16/19 (84.2%)

TABLE 2b

Parturition Summary for 22 Non-Vaccinated Control Mares Following Intranasal challenge Inoculation with EHV-1 Subtype 1 Virus

| Mare No. | Foaling Date | Days Post Challenge | Type Delivery | Foal Delivery Status | Cause of Death |
|---|---|---|---|---|---|
| 830 | 3-8-92 | 20 | Abortion | Dead | EHV-1 |
| 845 | 3-14-92 | 26 | Abortion | Dead | EHV-1 |
| 831 | 3-15-92 | 27 | Abortion | Dead | EHV-1 |
| 817 | 4-3-92 | 46 | Normal | Live | N/A |
| 825 | 4-4-92 | 47 | Normal | Live | N/A |
| 819 | 4-9-92 | 52 | Normal | Live | N/A |
| 741 | 4-10-92 | 53 | Normal | Live | N/A |
| 801 | 4-10-92 | 53 | Normal | Live | N/A |
| 838 | 4-10-92 | 53 | Normal | Live | N/A |
| 796 | 4-11-92 | 54 | Abortion | Dead | EHV-1 |
| 809 | 4-11-92 | 54 | Normal | Live | N/A |
| 752 | 4-12-92 | 55 | Abortion | Dead | EHV-1 |
| 822 | 4-12-92 | 55 | Normal | Live | N/A |

TABLE 2b-continued

Parturition Summary for 22 Non-Vaccinated Control Mares Following Intranasal challenge Inoculation with EHV-1 Subtype 1 Virus

| Mare No. | Foaling Date | Days Post Challenge | Type Delivery | Foal Delivery Status | Cause of Death |
|---|---|---|---|---|---|
| 861 | 4-13-92 | 56 | Normal | Live | N/A |
| 802 | 4-15-92 | 58 | Abortion | Dead | EHV-1 |
| 836 | 4-20-92 | 63 | Normal | Live | N/A |
| 811 | 4-23-92 | 67 | Normal | Live | N/A |
| 858 | 4-26-92 | 69 | Normal | Live | N/A |
| 842 | 5-1-92 | 77 | Normal | Live | N/A |
| 828 | 5-4-92 | 74 | Abortion | Dead | EHV-1 |
| 859 | 5-13-92 | 86 | Normal | Live | N/A |
| 857 | 5-15-92 | 88 | Normal | Live | N/A |

The Mean Days Post Challenge for foaling was 56, the Range varied from 20 to 83 days. Abortions/Deaths due to EHV-1 were 7/22 (31.8%).
Normal Foals: 15/22 (68.2%)

Example 2

Serial EHV-1 MHD 91-001 as described in Example 1 was tested in a vaccination/challenge study for its ability to protect young seronegative weanlings from respiratory disease caused by EHV-4. Twenty EHV-1 and EHV-4 seronegative naive weanling horses were used in this study. All horses were foaled and held isolated, and thus had no previous exposure to either EHV-4 or EHV-1. One month prior to the first vaccination and on the day of the first vaccination, all of the weanlings were bled to confirm that all were seronegative. Ten of the weanlings were vaccinated with a 1 mL dose of the EHV-1 monovalent vaccine EHV-1 MHD 91-001. Twenty-eight days after the first vaccination a 1 mL booster dose was administered to the vaccinated weanlings. Fourteen days post booster all weanlings were challenged with a heterologous EHV-4 strain designated T446. All weanlings were observed for clinical signs of EHV-4 respiratory disease for 11 days post challenge. Each weanling was challenged intranasally with $10^{4.0}$ $TCID_{50}$ of the EHV-4 virus using the nebulizer previously described.

Clinical signs of respiratory disease were indicated by observation of nasal exudates and an elevated temperature. Nasal exudates were scored daily by a single individual to maintain consistency of observations. Scoring grades of 0 to 6 were assigned on the basis of the severity of the disease. A score of 4 or greater was determined to be indicative of significant respiratory disease. Additionally, blood samples were drawn for evaluation of the WBC count and serological titer responses and nasal swab samples were taken for virus isolations.

Virus isolation and nasal exudate results are shown in Tables 3a and 3b and serological results are listed in Table 4. Temperature responses were significant as were the white blood cell counts. This is not unusual for respiratory disease associated with EHV-4.

There was a difference in virus shedding as determined by virus isolations from nasal swabs (Table 3a). A mean number of 6.7 non-vaccinated controls shed virus in their nasal exudates over the 11 day Post Challenge period whereas a mean number of 3.4 vaccinates shed virus. This was a 52% reduction in virus shedding.

The difference in nasal exudate scores between vaccinates and non-vaccinated controls was statistically significant (Table 3b). Eighty percent of the non-vaccinated control animals demonstrated nasal exudate scores >4 which indicated severe respiratory disease whereas only 20% of the vaccinated animals demonstrated nasal exudate scores >4. This represents a 75% reduction of respiratory disease in the vaccinates. Of even greater importance is the fact that the vaccinates only demonstrated 2 days of nasal exudate scores >4 whereas non-vaccinated controls demonstrated 10 days of nasal exudate scores >4.

Table 4 shows the serological response (serum neutralization titer) of the weanlings post vaccination, day of booster, day of challenge and 14 days post challenge. As proof that there was no pre-exposure to either EHV-4 or EHV-1 prior to challenge, the non-vaccinated controls remained seronegative for both virus subtypes. All weanlings did demonstrate positive serological titers to EHV-4 post challenge. Unlike reports by other scientists, all the vaccinated weanlings except one developed both EHV-1 and EHV-4 serum neutralizing titers as a result of either the first or second vaccination. This confirms that this EHV-1 monovalent vaccine is effective in producing serological responses to both EHV-1 and EHV-4.

The general decline of EHV-1 and EHV-4 serum neutralization titers 14 days post challenge inoculation suggests that the EHV-4 challenge virus is neutralizing both the EHV-1 and EHV-4 antibodies which were developed by the monovalent EHV-1 vaccine.

In summary, it has been demonstrated that the monovalent EHV-1 vaccine of this invention produces protection against an EHV-4 respiratory challenge and produces a serological response to both EHV-1 and EHV-4 in weanling horses which were not pre-exposed to either virus subtype.

TABLE 4a

Table 4a & 4b EHV-1 and EHV-4 Serum Neutralization Titers Recorded for 10 Vaccinated and 10 Non-Vaccinated Control Weanlings Collected Pre and Post Vaccination and Pre and Post Challenge Inoculation with EHV-1 Virus

| Test Virus | Vacc No. | Pre V1 | Pre V2 | Day of Chall | 14 Day Post Chall | Control No. | Pre V1 | Pre V2 | Day of Chall | 14 Day Post Chall |
|---|---|---|---|---|---|---|---|---|---|---|
| EHV-1 | 1011 | <2 | <2 | 5 | 4 | 1007 | <2 | <2 | <2 | <2 |
| | 1012 | <2 | <2 | 3 | 3 | 1010 | <2 | <2 | <2 | <2 |
| | 1017 | <2 | 8 | 6 | 2 | 1014 | <2 | <2 | <2 | <2 |
| | 1018 | <2 | 3 | 9 | 6 | 1015 | <2 | <2 | <2 | <2 |
| | 1021 | <2 | <2 | 10 | 6 | 1016 | <2 | <2 | <2 | <2 |
| | 1023 | <2 | <2 | 7 | 6 | 1025 | <2 | <2 | <2 | <2 |
| | 1024 | <2 | 3 | 21 | 9 | 1027 | <2 | <2 | <2 | <2 |
| | 1029 | <2 | <2 | 5 | 3 | 1028 | <2 | <2 | <2 | <2 |
| | 1030 | <2 | 2 | 32 | 16 | 1032 | <2 | <2 | <2 | <2 |
| | 1037 | <2 | <2 | 22 | 10 | 1033 | <2 | <2 | <2 | <2 |
| | GMT | <2 | 2 | 9 | 5 | GMT | <2 | <2 | <2 | <2 |

GMT = Geometric Mean Titer
V1 = Vaccination 1; V2 = Vaccination 2

TABLE 3a

EHV-4 Respiratory Disease -- Virus Isolation from Nasal Swabs
DAYS POST CHALLENGE
Number of Weanlings Shedding Virus on Each Day Post Challenge

| GROUP | -2 | -1 | 0 | 1 | 2 | 3 | 4 | 5 | 6 | 7 | 8 | 9 | 10 | 11 | Mean No. Of Animals with Virus Isolation |
|---|---|---|---|---|---|---|---|---|---|---|---|---|---|---|---|
| Vaccinates | 0 | 0 | 0 | 5 | 5 | 5 | 3 | 3 | 1 | 4 | 4 | 1 | 2 | 0 | 3.4 |
| Controls | 0 | 0 | 0 | 9 | 6 | 6 | 10 | 9 | 9 | 7 | 7 | 3 | 8 | 0 | 6.7 |

Mean Days of Virus Isolation for Vaccinates = 3.4 (30.9%)
Mean Days of Virus Isolation for Non-Vaccinated Controls = 6.7 (60.9%)
50% Reduction in Mean Days of Virus Isolation TABLE 3b EHV-1 Respiratory Disease -- Nasal Exudate Score >4
DAYS POST CHALLENGE
Number of Weanlings with Nasal Exudate Scores >4 for Each Day

| GROUP | -2 | -1 | 0 | 1 | 2 | 3 | 4 | 5 | 6 | 7 | 8 | 9 | 10 | 11 | No. >4* Total No. Weanlings |
|---|---|---|---|---|---|---|---|---|---|---|---|---|---|---|---|
| Vaccinates | 0 | 0 | 0 | 0 | 0 | 0 | 0 | 2 | 1 | 0 | 0 | 0 | 0 | 0 | 2/10 |
| Controls | 0 | 0 | 0 | 1 | 4 | 1 | 6 | 5 | 3 | 3 | 1 | 2 | 4 | 0 | 8/10 |

80% of the Non-Vaccinated Controls demonstrated significant Nasal Exudate Scores
20% of the Vaccinates demonstrated significant Nasal Exudate Scores.

TABLE 4b

| Test Virus | Vacc No. | Pre V1 | Pre V2 | Day of Chall | 14 Day Post Chall | Control No. | Pre V1 | Pre V2 | Day of Chall | 14 Day Post Chall |
|---|---|---|---|---|---|---|---|---|---|---|
| EHV-4 | 1011 | <2 | <2 | 32 | 24 | 1007 | <2 | <2 | <2 | 5 |
|  | 1012 | <2 | <2 | 7 | 4 | 1010 | <2 | <2 | <2 | 4 |
|  | 1017 | <2 | 4 | 13 | 5 | 1014 | <2 | <2 | <2 | <2 |
|  | 1018 | <2 | 3 | 29 | 14 | 1015 | <2 | <2 | <2 | 4 |
|  | 1021 | <2 | 3 | 48 | 12 | 1016 | <2 | <2 | <2 | 4 |
|  | 1023 | <2 | 3 | 197 | 6 | 1025 | <2 | <2 | <2 | 6 |
|  | 1024 | <2 | 3 | 11 | 11 | 1027 | <2 | <2 | <2 | 4 |
|  | 1029 | <2 | <2 | 6 | 4 | 1028 | <2 | <2 | <2 | 2 |
|  | 1030 | <2 | 2 | 37 | 16 | 1032 | <2 | <2 | <2 | 6 |
|  | 1037 | <2 | <2 | 15 | 11 | 1033 | <2 | <2 | <2 | 6 |
|  | GMT | <2 | 2 | 18 | 9 | GMT | <2 | <2 | <2 | 6 |

GMT = Geometric Mean Titer
V1 = Vaccination 1: V2 = Vaccination 2

The invention being thus described, it will be obvious that the same may be varied in many ways. Such variations are not to be regarded as a departure from the spirit and scope of this invention, and all such modifications are intended to be included within the scope of the following claims.

What is claimed:

1. A monovalent EHV-1 vaccine which provides protection against diseases associated with EHV-1 and EHV-4 comprising an EHV-1 virus represented by strain AB69 which is designated as ATCC VR-2581.

2. The vaccine according to claim 1 which provides protection against respiratory disease caused by both EHV-1, EHV-4 and the combination thereof.

3. A method of preparing the vaccine according to claim 1, comprising the steps of:
   a. infecting a susceptible cell line with an EHV-1 virus comprising an EHV-1 virus represented by strain AB69 or its equivalent which is designated as ATCC VR-2581;
   b. allowing said EHV-1 virus to grow in a growth-supporting media until a significant CPE is produces;
   c. harvesting said growth-supporting media containing said EH-1 virus, dead cells, cell debris and infected cells to produce a harvest material;
   d. inactivating said harvest material with a suitable inactivating agent; and
   e. adjuvanting said inactivated harvest material.

4. The method according to claim 3, wherein said cell line is an equine cell line.

5. The method according to claim 4, wherein said equine cell line is selected from the group consisting of an equine dermal cell line, an equine kidney cell line and an equine fetal lung cell line.

6. The method according to claim 3, wherein the inactivating agent is selected from the group consisting of beta propiolactone, formalin and binary ethylenimine.

7. The method according to claim 3, wherein the adjuvant is selected from the group consisting of Havlogen®, Carbopol 934P®, Polygen™, block copolymers, polymers, oils, aluminum salts, cytokines, immunomodulators and combinations thereof.

8. The method according to claim 4, wherein a stabilizer is added to the vaccine.

9. The method according to claim 4, wherein said harvest material is purified prior to inactivating.

10. The method according to claim 9, wherein said purification comprises filtering, ultrafiltering, column chromatographing or combinations thereof.

11. The method according to claim 3, wherein said harvest material is concentrated prior to inactivating.

12. A process for protecting a horse against diseases associated with EHV-1, EHV-4 or a combination thereof comprising administering to the horse a vaccine as recited in claim 1.

* * * * *